United States Patent [19]
Hollis et al.

[11] Patent Number: 5,554,510
[45] Date of Patent: Sep. 10, 1996

[54] REGULATION OF GENE EXPRESSION

[75] Inventors: Melvyn Hollis; David Pioli, both of Alderley Edge, United Kingdom; Dario Valenzuela, Somerville, Mass.

[73] Assignees: Imperial Chemical Industries, PLC, London, England; President and Fellows of Harvard College, Cambridge, Mass.

[21] Appl. No.: 161,170

[22] Filed: Dec. 1, 1993

Related U.S. Application Data

[63] Continuation of Ser. No. 20,231, Feb. 19, 1993, abandoned, which is a continuation of Ser. No. 573,159, filed as PCT/GB89/00334, Mar. 31, 1989, published as WO89/09256, Oct. 5, 1989, abandoned.

[30] Foreign Application Priority Data

Mar. 31, 1988 [GB] United Kingdom ............... 8807683

[51] Int. Cl.$^6$ .......................... C12N 15/09; C12N 15/67
[52] U.S. Cl. ................ 435/69.1; 435/172.1; 435/172.3; 435/240.1; 435/252.3; 435/254.2; 435/254.21; 435/320.1; 536/23.1; 536/24.1; 935/33
[58] Field of Search ................... 435/69.1, 71.1, 435/71.2, 91.1, 172.3, 320.1, 240.1, 252.3, 254.2, 254.211; 530/350; 536/23.1, 24.1; 935/33

[56] References Cited

PUBLICATIONS

Hu and Davidson, *Cell* (1987) 48:555–566.
Brown et al., *Cell* (1987) 49:603–612.
Hu and Davidson, *Gene* (1988) 62:301–313.
Hollis et al., *Proc. Natl. Acad. Sci.* (1988) 85:5834–5838.
Koudelka et al., *Nature* (1987) 326:886–888.
Turner and Tjian, *Science* (1989) 243:1689–1694.
Wharton and Ptashne, *Nature* (1985) 316:601–605.
Wharton and Ptashne, *Nature* (1987) 326:888–891.
Lin et al., *Cell* (1988) 54:659–664.
Brent and Ptashne, *Cell* (1985) 43:729–736.
Brent and Ptashne, *Nature* (1984) 312:612–615.
Smith et al., *EMBO J.* (1988) 7:3975–3982.
Miller et al., "Identification and comparison of two sequence elements that confer cell–type specific transcription in yeast," (Apr. 18, 1985) *Nature*, 314:598–603.
Bender et al, "MATα1 Protein, a yeast transcription activator, binds synergistically with a second protein to a set of cell–type–specific genes," (Aug. 28, 1987) *Cell*, 50:681–691.
Olesen et al, "Yeast HAP2 and HAP3 activators both bind to the *CYC1* upstream activation site, UAS2, in an interdependent manner," (Dec. 24, 1987) *Cell*, 51:953–961.
Chodosh et al, "A yeast and a human CCAAt–binding protein have heterologous subunits that are functionally interchangeable," (Apr. 8, 1988) *Cell*, 53:25–35.
Ptashne et al. A Genetic Switch: Gene Control & Phage λ. pp. 98–99. 1987. Cell Press. Maniatis 1982. Molecular Cloning CSH.
Webster et al. Mol. Microbiol. (1992) 6:371–377.
Thliveris et al. Biochimie (1991) 73:449–455.

*Primary Examiner*—John L. LeGuyader
*Attorney, Agent, or Firm*—Morrison & Foerster

[57] ABSTRACT

The present invention relates to the regulation of gene expression which entails providing a pair of unlike proteins, with unlike DNA binding domains, which will associate to form a heterodimer and bind to appropriate asymmetric DNA binding sites and hence depress or increase expression of adjacent genes.

10 Claims, 5 Drawing Sheets

REGULATION OF GENE EXPRESSION

This application is a continuation of application Ser. No. 08/020,231, filed Feb. 19, 1993, now abandoned, which is a continuation of Ser. No. 07/573,159, filed as PCT/GB89/00334 on Mar. 31, 1989, published as WO89/09256 on Oct. 5, 1989, now abandoned.

BACKGROUND OF THE INVENTION

This invention relates to the regulation of gene expression.

In living systems much of the work of the cell is carried out by proteins according to the blue-print specified in the cell's genome. Genetic engineering can alter the working of the cell, using recombinant DNA techniques, in two main ways. Firstly, it can modify the type of proteins the cell produces, either by modifying the DNA code for production of a particular protein, or by altering or deleting the code (so that that protein is no longer produced) or by inserting entirely new code segments (so as to produce a protein that is not normally found in the cell at all). Secondly, in some cases it is possible, by changes to the DNA in the neighbourhood of that which codes for the protein, to increase or reduce the amount of protein produced by the code, or to change the circumstances which cause the cell to produce the protein.

The present invention relates primarily to techniques of the second type, and provides means whereby the production of proteins by the cell may be more readily regulated as may be desired.

It is well-known that genes have a regulatory region, which controls their expression. Typically, regulation is by means of binding of a protein present in the cell onto a short DNA sequence (binding site) upstream of the start of transcription. Binding of the protein onto the binding site may either inhibit or promote expression of the downstream gene. The mechanisms vary: in some cases the bound molecule may overlap or occupy the site needed by RNA polymerase to initiate messenger RNA production, so that expression is inhibited; in other cases the bound protein may prevent binding of a different protein which would have an inhibiting effect. Alternatively, binding of the protein may facilitate RNA polymerase binding thereby stimulating gene expression. The classic case of gene regulation is that of the bacteriophage lambda repressor which binds to specific DNA sequences on the lambda genome and, under the appropriate physiological conditions, can repress or activate gene expression. There are a number of examples in the literature (e.g. Brent, R. and Ptashne, M. (1985), Cell 43, 729–736), which show that DNA binding, protein dimerisation and gene modulation are separable functions.

One class of protein regulators comprises those which bind to double-stranded DNA as dimers. They comprise discrete domains. Part of one such domain is cognate to a specific DNA site (defined by a specific sequence of bases, the exact nature of some of which are essential and some optional), recognising or interacting with it. Whilst bases in either strand may be involved in contacts with the DNA binding domain of the protein, the protein binding site can be unambiguously defined by the base sequence of either DNA strand within that protein binding site. Two such protein monomers in the form of a dimer will bind to a locus comprising two such sites. A single such site is insufficient for binding of either the dimer or the monomer. The sites are adjacent, and generally have identical or similar defining sequences, but on complementary strands of the DNA. The two similar DNA defining sequences on the complementary strands thus have opposite orientation in space. The binding locus or site defined by the adjacent DNA sequences accordingly has two-fold rotational symmetry.

It might in principle be possible to use such dimers to engineer artificial regulation of gene expression but this would be subject to disadvantages. Such symmetrical DNA sequences (which may, for example, be twenty to thirty base-pairs long) are relatively rare in nature. It may be awkward or inconvenient to insert such sequences into the genome of the organism. Moreover, control of gene expression will be limited. It will be dependent on only one factor, namely the concentration in the cell of the protein monomer. The use of bacterial repressor homodimers to regulate expression of artificially engineered genes introduced into yeast, mammalian and invertebrate cells has already been demonstrated, Brent, R. and Ptashne, M. (1984) Nature, 312, 612–615, Smith, G. M. et al, (1988), EMBO J., 7, 3975–3982; Hu, M. C.-T. and Davidson, N. (1987), Cell, 48, 555–566; Brown, M. et al, (1987), Cell, 49, 603–612; Hu, M. C.-T and Davidson, N. (1988), Gene, 62, 301–313. In these situations the use of heterodimers for control would have advantages due to the control which can be exerted by variation in the levels of production of either protein monomer (see later). In these cases the control of gene expression by the homodimer or the heterodimer is dependent upon the introduction of the appropriate binding site(s) upstream of the target gene. There are situations where this is not currently feasible for technical reasons (e.g. in hexaploid plants where six gene copies need to be altered in the same cells) or for ethical reasons (e.g. in the genomes of humans) and in these situations, control by heterodimers is a more attractive and realistic alternative. Since the heterodimers do not require dyad symmetry, any stretch of the appropriate number of bases of double-stranded DNA can be regarded as a binding site for a heterodimer with sites for the individual monomers being adjacent and on complementary strands of the double-stranded DNA. Thus by appropriate choice of binding specificities, the appropriate heterodimer can be directed, in principle, to any specific DNA sequence in the controlling regions of the target genes, without modifying the gene itself. For example, the sequence of the human corticotropin releasing factor gene contains the DNA sequence 5'ATTCAAGAATTTTGT3' at position 49 (in the published squence; ref. HUMCRF in the Genbank Database) which is a binding site for the heterodimer described in detail in this Specification.

SUMMARY OF THE INVENTION

The present invention bases itself on our idea that it would be possible to provide a pair of unlike proteins, with unlike DNA binding domains, which will nevertheless associate to form a heterodimer and bind to appropriate asymmetric DNA binding sites and hence may be used to regulate expression of adjacent genes.

Thus, according to the present invention we provide a cell comprising a gene capable of expressing a functional protein: a regulatory region for said gene operatively associated therewith; a protein-binding site within said regulatory region defined by adjacent different first and second DNA sequence on complementary strands: a first protein monomer having a first DNA-binding domain cognate to said first DNA sequence; and a second protein monomer having a second DNA-binding domain cognate to said second DNA sequence; said first and second protein monomers being capable of association to form a heterodimer: whereby said heterodimer may bind to said protein-binding site and thereby regulate expression of said gene: said first and second DNA-binding regions and said first and second DNA sequences differing substantially so that said protein-binding site lacks rotational symmetry.

Definitions

For the purposes of this Patent:

ASSOCIATION the ability to form protein dimers from compatible monomers through non-covalent interactions; for example electrostatic interactions, Van der Waal's forces.

DIFFERENT with respect of DNA sequences present on complementary strands within a DNA binding site means lacking rotational symmetry.

COGNATE A particular DNA binding domain in a protein monomer contains the requisite specificity (within its amino acid sequence) for recognising a particular DNA site (defined by the DNA sequence on one strand) and is therefore COGNATE to that site. Although cognate, the protein monomer is actually incapable of specific binding unless the DNA binding domain is presented as a dimer in the correct configuration to bind simultaneously to a site containing the corresponding DNA sequences in opposite orientations on complementary strands.

We further provide the method of regulating gene expression in a cell, which cell comprises: a gene capable of expressing a functional protein: a regulatory region operatively associated with said gene; and a protein-binding site within said regulatory region defined by adjacent different DNA sequences on complementary strands; the method comprising supplying in the cell first and second different protein monomers each comprising a first and a second different DNA-binding domains, respectively, said monomers being capable of forming a heterodimer that can bind to said protein-binding site and regulate expression of the functional protein.

The invention also includes a recombinant gene system comprising: a gene for expressing a functional protein; a regulatory region operatively associated with said gene; and a protein-binding site within said regulatory region; the protein-binding site being defined by adjacent different first and second DNA sequences on complementary strands for binding to first and second dissimilar regulator proteins that, when so bound, regulate expression of the functional protein.

In each case, regulation of gene expression may mean either promotion or inhibition of production of functional protein. Generally the regulatory region is upstream of the gene, though occasionally it is downstream or within the gene itself.

In accordance with our invention neither protein monomer binds to its cognate protein-binding site in the heterodimer binding site in the absence of the other; there is no gene regulation unless both proteins are present.

DETAILED DESCRIPTION OF THE INVENTION

Our invention has two significant advantages. Firstly, because it does not require a symmetric DNA binding site in the regulator region, it opens the possibility for considerably wider application in the regulatory regions of existing genes (using modified binding proteins rather than inserting or changing DNA sequences in such regulator regions). Secondly, it provides for expression to be regulated directly in response to two different factors—and indirectly, as will be shown, in response to any desired combination of factors.

Each component of the heterodimer is a protein which is itself produced by a gene. Each such gene may itself be regulated, either in response to an extrinsic factor (e.g. presence of a small molecule such as ethylene; or temperature) or in response to a regulator protein. This regulator protein may be a different homodimer, a second heterodimer or the same heterodimer (autoregulation). The second heterodimer may be regulated similarly. In this way, one can see how as many control factors as desired could, in principle, be used to regulate expression of the target gene. Naturally, for each control factor an appropriate regulatory DNA sequence recognising it must be available. As regulation can be made either to promote or inhibit expression, expression of the target gene can be made dependent upon the presence or absence of two or more control factors, or any combination of them. This is a distinct advantage over control by a homodimer, since this is the product of a single gene.

Accordingly, our invention further provides a genome of a prokaryotic or eukaryotic organism comprising: a first gene for expressing a functional protein; a first regulatory region operatively associated with said gene; and a protein-binding site within said first regulatory region; the protein-binding site being defined by adjacent different first and second DNA sequences on complementary strands: a second gene for expressing a first protein monomer, said protein comprising a first DNA-binding domain cognate to said first DNA sequence; and a third gene for expressing a second protein monomer, said protein comprising a second DNA-binding domain cognate to said second DNA sequence; whereby expression of said second and third genes may serve to regulate expression of said first gene.

Said genome may have a second regulatory region provided usually upsteam of said second gene, said second regulator region serving to regulate production of said first protein monomer in response to the presence or absence of one or more regulators.

Said genome may further have a third regulatory region provided usually upstream of said third gene, said third regulatory region serving to regulate production of said second protein monomer in response to the presence or absence of one or more regulators that may be the same as or different from the regulator influencing the second regulatory region.

Moreover, at least one of said regulator molecules may be a protein molecule produced by a recombinant gene system according to the invention.

Our invention further comprises a novel heterodimer regulatory protein formed by association of differing first and second protein monomers comprising different first and second DNA-binding domains respectively; which heterodimer is capable of binding to a protein-binding site defined by adjacent different first and second DNA sequences, cognate to said first and second DNA-binding domains. Specific heterodimers of the invention are those wherein the first DNA binding site is cognate to the DNA sequence:

5'AXTXAAGXX3' and wherein the second DNA binding site is cognate to the DNA sequence:

5'ACAAXXX3' where X is a nucleotide base A,T,C or G, and more particularly wherein the first DNA binding site is cognate to the DNA sequence:

5'ATTTAAGTT3' and wherein the second DNA binding site is cognate to the DNA sequence:

5'ACAATAA3'.

The invention also extends to specific protein binding sites lacking rotational symmetry comprising the DNA sequence

5'AXTXAAGXXXXXTTGT3' where X is a nucleotide base, A,T,C or G; or a complement thereof, and more particularly, the DNA sequence

5'ATTTAAGTTTTATTGT3' or a complement thereof. Such protein binding sites lacking rotational symmetry may occur naturally in a DNA sequence including a gene to be expressed under the influence of a regulator region but, in principle, such protein binding sites can also be introduced synthetically as foreign DNA into a DNA sequence including a gene to be expressed under the influence of a regulator region. In this way, the modified gene contains a known protein binding site lacking rotational symmetry onto which the appropriate binding heterodimer can bind.

Our invention is of quite general applicability, but will be further illustrated by specific reference to the bacteriophage 434 repressor protein.

The bacteriophage 434 protein binds to specific DNA sequences (the 434 operators) by the insertion of an alpha helix (recognition helix) into the major groove of B-form DNA (Anderson et al, 1987). This recognition helix is part of a conserved 'helix-turn-helix' structure which is seen in many prokaryotic and some eukaryotic DNA-binding proteins (Sauer et al, 1982; Pabo and Sauer, 1984). A number of experiments have demonstrated that the sequence specificity of DNA-binding resides in the amino acid sequence of the outer (solvent exposed) face of the recognition helix of the repressor proteins. Wharton and Ptashne (1985) were able to change the specificity of the bacteriophage 434 repressor to that of the P22 repressor by substituting the exposed residues of the 434 recognition helix for those of the P22 repressor. The new protein named 434R [alpha 3 (P22R)] is identical to 434 repressor except for four amino acids on the solvent exposed side of the recognition helix. The DNA binding specificity of the new protein is such that it recognises only P22 operators and not 434 operators. This is outlined schematically in FIG. 1.

Figure 1:
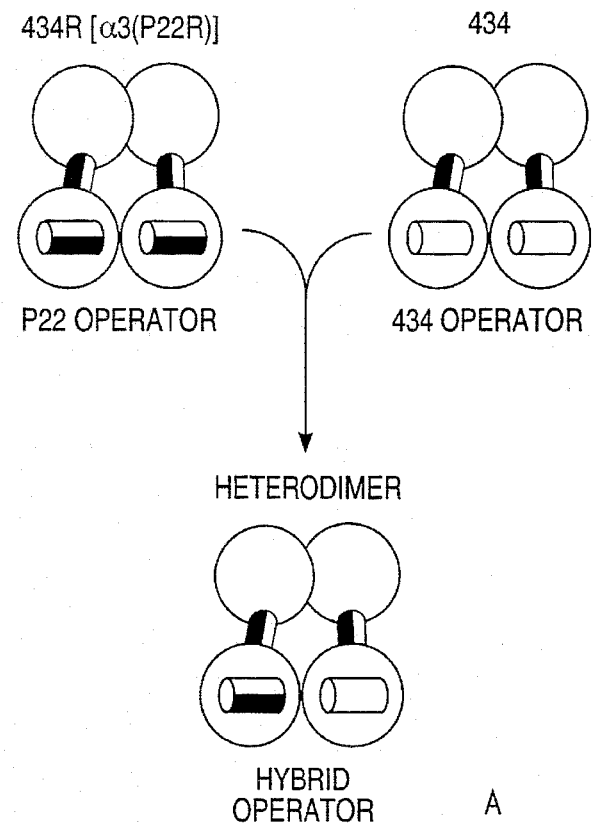
FIG. 1 represents schematically the heterodimer and binding site according to the present invention, and shows its relation to known dimer/binding site complexes.

In FIG. 1, the 434 repressor protein is shown bound as a homodimer to operator DNA using helix 3. When the solvent exposed residues of 434 repressor helix alpha 3 were substituted by those of P22 repressor (shown black), the resulting repressor binds only to P22 operators (Wharton and Ptashne, 1985). Since 434 repressor and 434R [alpha 3 (P22R)] repressor are identical with respect to dimer contacts, they should be capable of forming a mixed dimer (a heterodimer) consisting of one monomer of each protein. Such a heterodimer should be capable of specifically recognising a hybrid operator which bears half of a 434 operator and half a P22 operator. This is schematically outlined in FIG. 1.

Figure 2A:
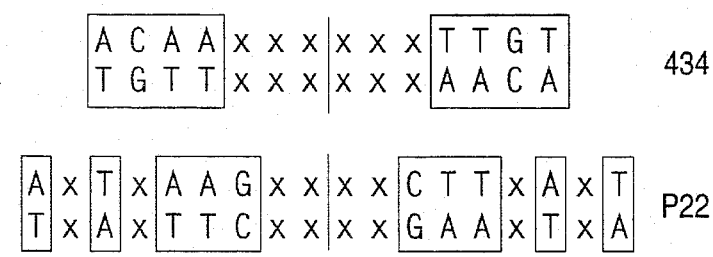
FIG. 2 represents the DNA sequences of two dyad symmetric operators (434 and P22) and three asymmetric hybrid sequences.
Figure 2B:
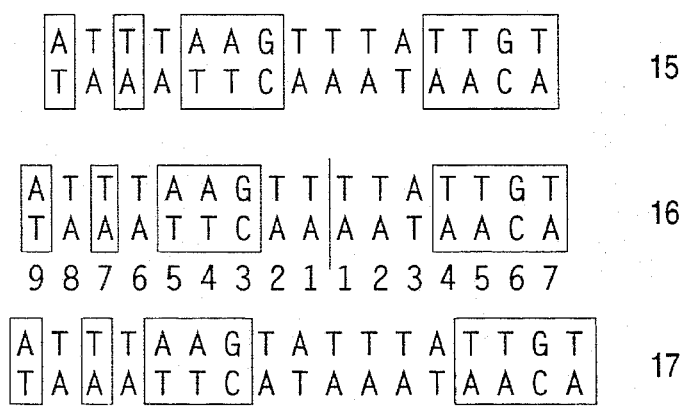

As shown in FIG. 1, 434 and 434R [alpha 3 (P22R)] repressors bind to 434 and P22 operators respectively. Since the only differences between these two proteins lie in the DNA-binding surface of the recognition helix, these proteins should be able to form heterodimers which should be capable of recognising a hybrid operator as shown. Such a hybrid operator has no dyad symmetry, a feature that is required for binding of the repressor homodimers. Since the two homodimer recognition sites are of different lengths (14 base pairs (bp) for 434 and 18 bp for P22) and since it was not clear that simply joining two half-operators would result in a functional heterodimer binding site, we constructed three potential binding sites. One of these sites (the 16 bp hybrid operator) was made by fusing a 434 half-site to a P22 half-site directly. The other two sites were identical to this fusion except that they contained either an insertion (17 bp site) or a deletion (15 bp site) of one base at the centre of 16 bp hybrid site. These sites are shown in FIG. 2, together with the 434 and P22 sites from which they are derived. In FIG. 2, where the sequences for the P22 and 434 operators are depicted only those bases which are thought to be essential to the binding function are shown. Other bases are indicated by "X".

The DNA sequences of the 15 bp, 16 bp and 17 bp hybrid operators are shown in FIG. 2. The 16 bp operator has one P22 half-site directly fused to a 434 half-site. The other two sites were made by the addition or subtraction of one base from the centre of the site.

The heterodimers were made in vitro by mixing 434 and 434R [alpha 3 (P22R)] repressors. The mixture was assayed for operator binding using a standard filter binding technique. Details are given below under Experimental Procedures. In brief, a short DNA sequence containing the operator of interest is radioactively labelled and mixed with increasing amounts of the protein preparation which is being assayed for operator binding. After a short incubation, the DNA and protein mixture is filtered through a nitrocellulose filter under conditions where protein is retained on the filter but DNA passes through. Any radioactive DNA which is specifically bound by the protein will also be retained on the filter and can be assayed by scintillation counting. The percentage of the radioactive DNA which is retained can therefore be used as a sensitive assay for protein/DNA binding.

Using the filter-binding assay, we initially determined that only the 16 bp hybrid operator site (with 434 and P22 half-sites exactly fused) was specifically retained by a mixture of 434 and 434R [alpha 3 (P22R)] repressors. We further determined that neither of the homodimers (434 or 434R [alpha 3 (P22R)] bound the 16 bp hybrid site. The repressor heterodimer binds specifically and with high affinity to the hybrid site. See FIG. 3 for filter-binding results.

Figure 3A:
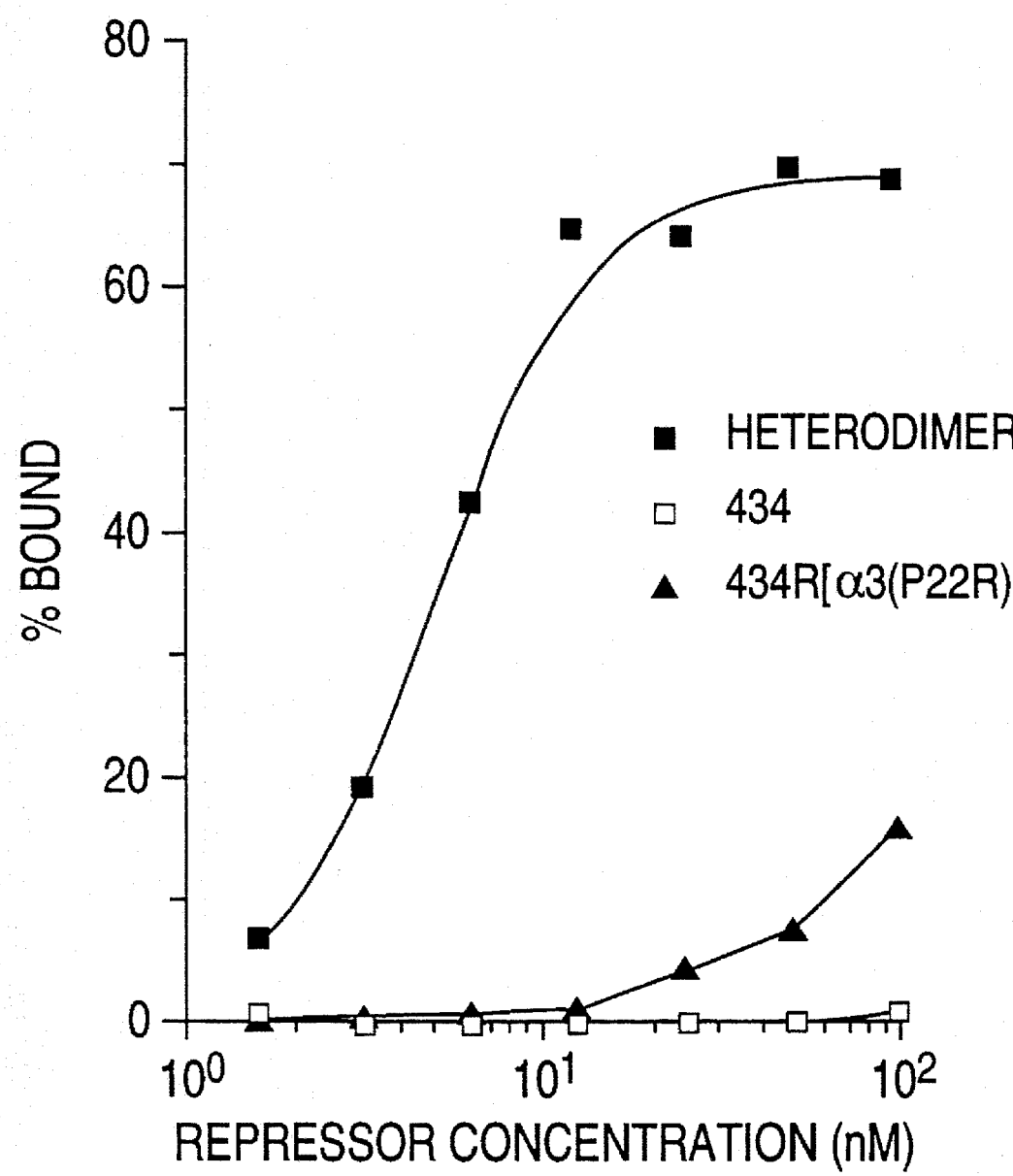
FIG. 3 shows graphically the results of filter binding experiments using radiolabelled 15, 16 and 17 basepair hybrid operators and various proteins.
Figure 3B:
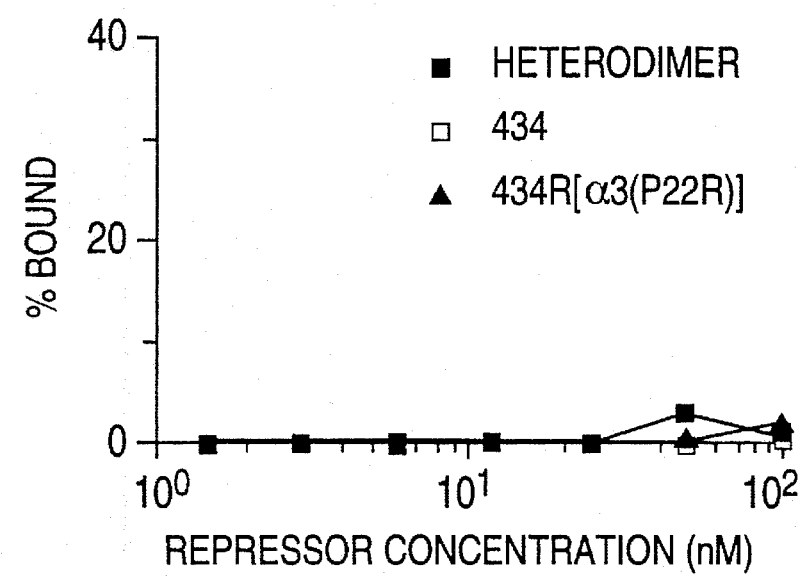
Figure 3C:
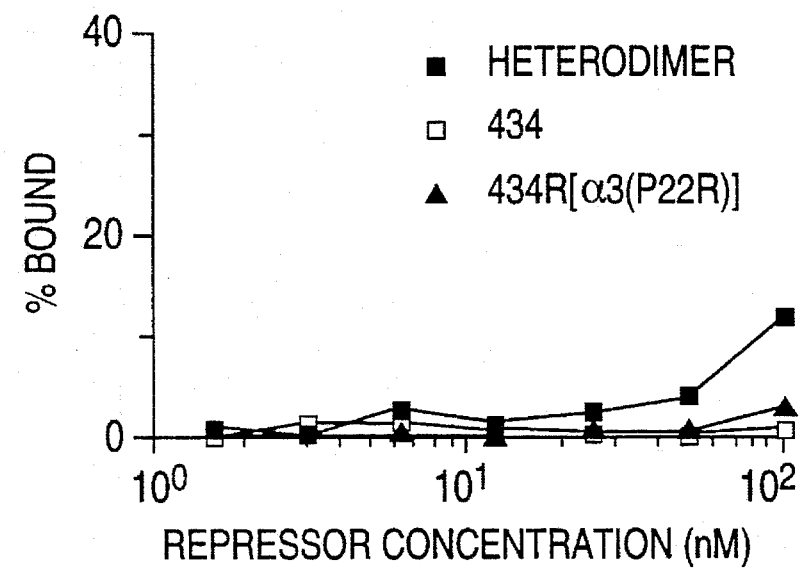
Figure 4:
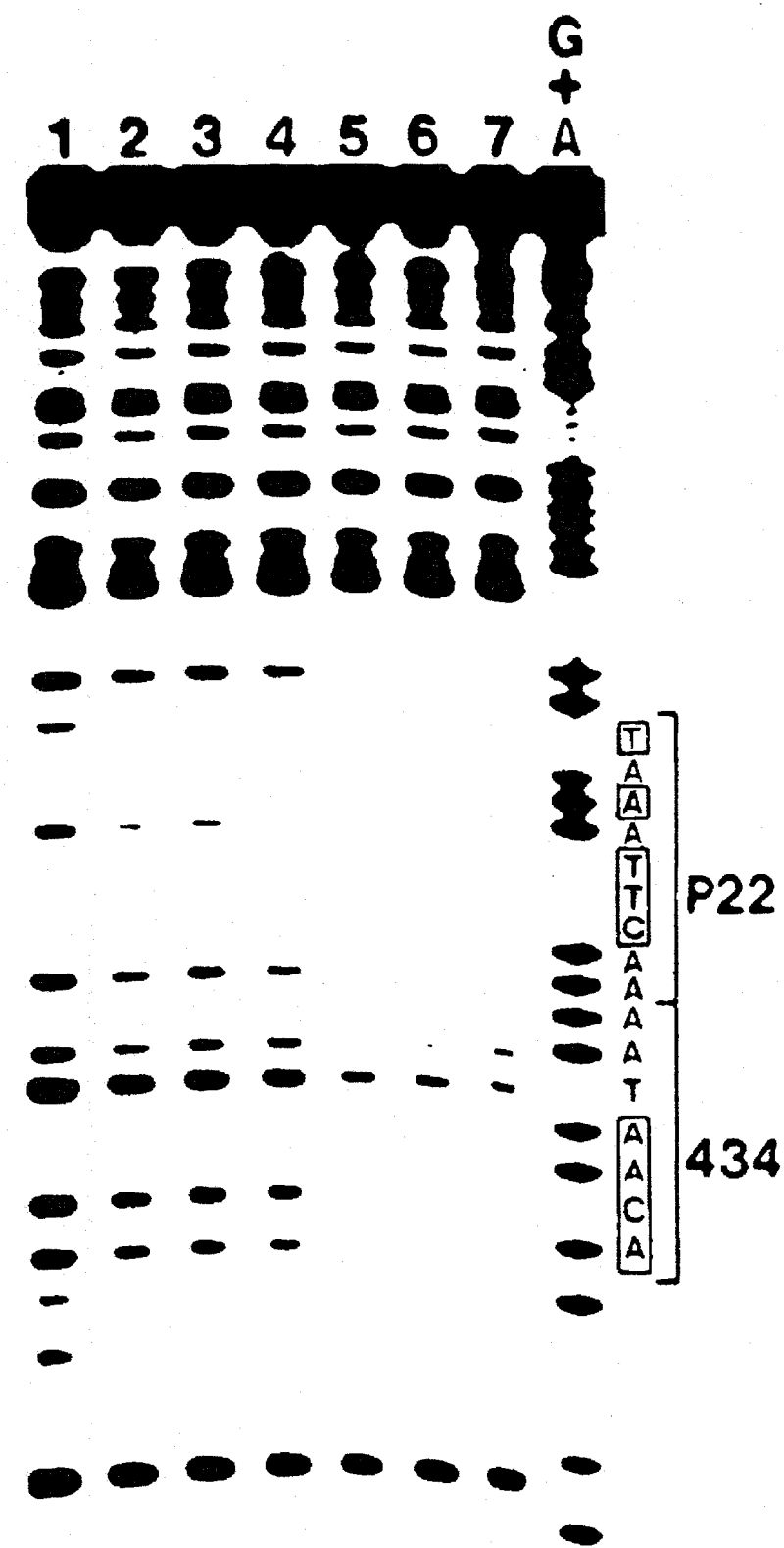
FIG. 4 comprises autoradiographs of radioactively labelled hybrid operator DNA after partial cleavage with DNaseI and electrophoresis.

FIG. 3 shows the results of filter binding experiments using radioactively labelled 15, 16 and 17 bp hybrid operator and various protein preparations. The results for the heterodimer were obtained using a 1:1 mixture of 434 and 434R [alpha 3 (P22R)] repressors, with or without pre-incubation to allow the formation of heterodimers before the addition of DNA. The results show, for the first time, that a heterodimer formed from two related monomers with distinct DNA binding specificities can bind to a hybrid operator site. The formation of the heterodimer generates a novel DNA binding specificity which is distinct from that of either of the repressor homodimers in the mixture.

Additional evidence for binding of the heterodimer to the hybrid recognition site was obtained from DNaseI protection experiments: these were carried out as described in Experimental Procedures. An EcoRI-HindIII fragment of plasmid pAD16 which carries the hybrid operator was 5'-end labelled at the HindIII site and incubated with serial dilutions of the mixed repressor preparation. The heterodimer concentrations in each reaction were LANE 1, no repressor; 2, 1.6 nM; 3, 3.1 nM; 4, 6.2 nM; 5, 12.5 nM; 6, 50 nM; 7, 100 nM. The lane marked A+G is the same DNA fragment cleaved at purines as described in Maniatis et al (1982). The sequence of the hybrid operator is as shown in FIG. 2 and the positions of the 434 and P22 half-sites on the fragment are marked. The results show that the repressor mixture recognises and binds to the operator specifically as expected. The size of the protected region (25 bp) corresponds to that seen for the binding of a single 434 or 434R [alpha3 (P22R)] repressor dimer to a single binding site (Wharton et al. 1984; Wharton and Ptashne, 1985). Under the same conditions, no footprint was seen for either 434 or 434R [alpha3 (P22R)] repressors alone (data not shown).

There are a number of ways in which novel specificity homodimers (and consequently novel specificity heterodimers) can be generated. These are summarised in FIG. 5. In brief, the specificity of the DNA binding protein can be altered, without grossly altering dimerisation, by specific changes to the DNA recognition helix, by random changes to the recognition helix or by completely replacing the DNA-recognition domain whilst retaining the dimerisation domain. In the simplest case, such as that used to generate the 434 (alpha3[P22R]) repressor which is used illustratively in this Specification, the residues which contact DNA from one repressor can be used to substitute for those of a second repressor (see Wharton and Ptashne, 1986). Homodimers with novel specificity can be made by a number of methods, for examples see Wharton and Ptashne, 1987; Youderian et al, 1983. The DNA binding specificity of the homodimer can also be altered by changing the DNA binding domain to that of another protein. This method was used by Lin et al, 1988, to generate a protein (GAL4 (1–74)+lambda R(112–236) ) which retains the dimerisation contacts of a bacterial repressor protein (lambda repressor) but has the DNA binding specificity of the yeast GAL4 protein.

Figure 5:
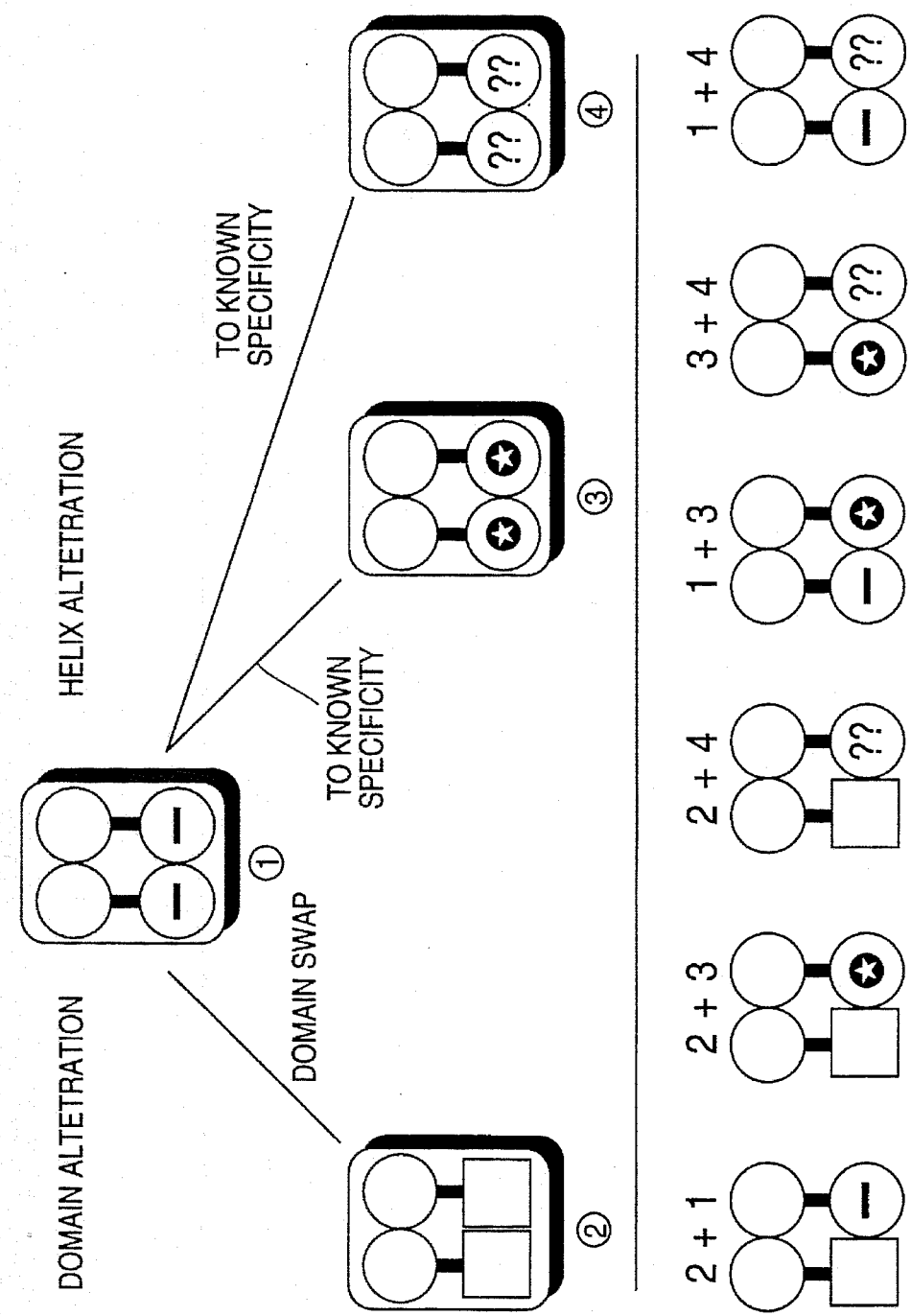
FIG. 5 summarises approaches available to generate a range of heterodimers that can be used in this invention.

Since the alterations in DNA binding specificity do not grossly alter the dimerisation domain of the repressor proteins, these altered specificity homodimers could then be used in combination with each other or with the parent homodimer to generate a range of heterodimers with novel specificities (see lower-half of FIG. 5).

EXPERIMENTAL PROCEDURES

Protein Purification

434R [alpha3 (p22R)] repressor was purified from cells carrying plasmid pRW219 as previously described (Wharton and Ptashne, 1985). 434 Repressor was purified by the method of Anderson et al (1984). Both proteins were assayed for activity and found to be >85% active.

Cloning of Hybrid Operators

Double-stranded synthetic oligonucleotides carrying the hybrid operators flanked by Sal 1 compatible ends were cloned into the Sal 1 site of plasmid puC18 to generate plasmids pAD15, pAD16 and pAD17. The polylinker region of plasmid pAD16 was recloned into plasmid pEMBL8+ (Dente et al, 1985) to give pDV50. Preparation of single stranded pDV50 DNA from E.coli strain RZ1032 (ATCC 39737; Kunkel, 1985) and subsequent mutagenesis were as described by Zoller and Smith (1982). All operator sequences were verified by plasmid sequencing using the method of Chen and Seeburg (1985).

Filter Binding

The hybrid operators were excised from the corresponding plasmids as approximately 80-bp EcoR1-HindIII fragments and were 5'-end labelled to high specific activity at either the EcoR1 or HindIII end using polynucleotide kinase and 32p-dATP as described (Maniatis et al, 1982). Nitrocellulose filter binding assays (Riggs et al, 1968) were as described below. The labelled operator fragments were incubated with the repressors at a final concentration of <20 pM in 400 ul of 50 mM sodium cacodylate (pH 8), 10 mm magnesium chloride, 0.1 mm disodium EDTA, 50 mm potassium chloride (CB buffer) containing 5 ug/ml sonicated chick blood DNA and 50 ug/ml BSA. 434 and 434R [alpha3 (P22R)] repressors were diluted on ice to a concentration of 1 uM in CB buffer (+BSA) and aliquots of the diluted proteins were mixed in equal proportions to give the 'heterodimer' sample. The three diluted protein samples were immediately added to parallel binding reactions to give a final range of repressor concentrations from 1.5 nM to 100 nM. After incubation at room temperature for 15 minutes to allow binding, the samples were filtered through 24 mm nitrocellulose filters (Millipore, type HA 0.45 um) which had been presoaked in CB buffer. The retention of labelled operator DNA was measured by Cerenkov counting of the filters. A sample without repressor was included to give a background retention (always less than 6%) which was subtracted from the measured values.

DNaseI Protection Experiments

DNaseI protection experiments were performed essentially as described by Johnson et al (1979) except that CB buffer containing 5 ug/ml sonicated chick blood DNA and 50 ug/ml BSA was used for repressor binding and DNaseI cleavage reactions. DNA fragments containing the hybrid operators were prepared and labelled as described above for filter binding.

REFERENCES

Anderson, J. E., Ptashne, M., and Harrison, S. C. (1987), Nature, 326, 846–852.
Pabo, C. O. and Sauer, R. T. (1984) Ann. Rev. Biochem. 53, 293–321.
Sauer, R. T., Yocum, R. R., Doolittle, R. F., Lewis, M. and Pabo, C. O. (1982), Nature, 298, 447–451.
Wharton, R. P. and Ptashne, M. (1985), Nature, 316, 601–605.
Anderson, I. E. (1984) The 7 Å Structure of a 434 Repressor-operator Complex (Ph.D. Thesis, Harvard University).
Dente, L. Cesareni, G. and Cortese, R. (1983) Nucleic Acids Res. 11, 1645–1655.

Kunkel, T. A. (1985) Proc. Natl. Acad. Sci. USA, 82, 488–492.

Wharton, R. P., Brown, E. L. and Ptashne, M. (1984) Cell, 38, 361–369.

Chen, E. Y. and Seeberg, P. H., (1985) DNA, 4, 165–170.

Riggs, A. D., Bourgeois, S., Newby, R. F., and Cohn, M., (1968) J. Mol. Biol. 34, 365–368.

Zoller, M. J., and Smith, M. (1982) Nucleic Acids Res. 10, 6487–6500.

Johnson, A. D., Meyer, B. J., and Ptashne, M. (1979) Proc. Natl. Acad. Sci. USA, 76, 5061–5065.

Maniatis, T., Fritsan, E. F. and Sambrook, J. (1982) "Molecular Cloning, A Laboratory Manual" (Cold Spring Harbor, N.Y.).

Lin, Y. S. et al, (1988) Cell, 54, 659–664.

Wharton, R. P. and Ptashne, M. (1986), Trends Biochem. Sci. 11, 71–73.

Wharton, R. P. and Ptashne, M. (1987), Nature, 326, 881–891.

Youderian et al, (1983), Cell, 35, 777–783.

We claim:

1. A regulated expression construct comprising a gene, said gene comprising:
   A) a first DNA sequence coding for a protein;
   B) a DNA regulatory region operatively associated with said first DNA sequence, said DNA regulatory region having a protein-binding site consisting of adjacent different second and third DNA sequences on complementary strands; wherein said protein binding site binds a heterodimer regulatory protein; wherein said heterodimer regulatory protein consists of different first and second protein monomers which do not naturally form a heterodimer; and wherein
      i) said first protein monomer has a DNA-binding domain cognate to said second DNA sequence;
      ii) said second protein monomer has a DNA-binding domain cognate to said third DNA sequence; and
      iii) wherein said first and second protein monomers associate to form said heterodimer regulatory protein;
   C) a fourth DNA sequence coding for said first protein monomer;
   D) a fifth DNA sequence coding for said second protein monomer;
   wherein upon expression of said fourth and fifth DNA sequences, said first and second protein monomers are made and associate to form said heterodimer, and wherein said heterodimer binds said regulatory region, thereby regulating expression of said first DNA sequence.

2. The expression construct of claim 1, wherein said first protein monomer has a DNA-binding domain cognate to said second DNA sequence, wherein said second DNA sequence has the DNA sequence:

5'AXTXAAGXX3' and wherein said second protein monomer has a DNA-binding domain cognate to said third DNA sequence, wherein said third DNA sequence has the DNA sequence:

5'ACAAXXX3' wherein X is a nucleotide base A, T, C or G.

3. The expression construct of claim 1, wherein said first protein monomer has a DNA-binding domain cognate to said second DNA sequence, wherein said second DNA sequence has the DNA sequence:

5'ATTTAAGTT3' and wherein said second protein monomer has a DNA-binding domain cognate to said third DNA sequence, wherein said third DNA sequence has the DNA sequence:

5'ACAATAA3' wherein X is a nucleotide base A, T, C or G.

4. The expression construct of claim 1 wherein said first or second protein monomer has a DNA-binding domain cognate to the DNA sequence:

5'AXTXAAGXXXXXTTGT3' where X is a nucleotide base A, T, C or G; or a complement thereof.

5. The expression construct of claim 4 wherein said DNA sequence is

5'ATTTAAGTTTTATTGT3'.

6. A host cell comprising a regulated expression construct, wherein said regulated expression construct comprises a gene, said gene comprising:
   A) a first DNA sequence coding for a protein;
   B) a DNA regulatory region operatively associated with said first DNA sequence, said DNA regulatory region having a protein-binding site consisting of adjacent different second and third DNA sequences on complementary strands; wherein said protein-binding site binds a heterodimer regulatory protein; wherein said heterodimer regulatory protein consists of different first and second protein monomers which do not naturally form a heterodimer; and wherein
      i) said first protein monomer has a DNA-binding domain cognate to said second DNA sequence;
      ii) said second protein monomer has a DNA-binding domain cognate to said third DNA sequence;
      iii) wherein said first and second protein monomers associate to form said heterodimer regulatory protein;
   C) a fourth DNA sequence coding for said first protein monomer;
   D) a fifth DNA sequence coding for said second protein monomer;
   wherein upon expression of said fourth and fifth DNA sequences, said first and second protein monomers are made and associate to form said heterodimer regulatory protein, and wherein said heterodimer binds said DNA regulatory region thereby regulating expression of said first DNA sequence.

7. The host cell of claim 6, wherein binding of said heterodimer to said regulatory region inhibits expression of said first DNA sequence.

8. The host cell of claim 6, wherein said first protein monomer has a DNA-binding domain cognate to said second DNA sequence, wherein said second DNA sequence has the DNA sequence:

5'AXTXAAGXX3' and wherein said second protein monomer has a DNA-binding domain cognate to said third DNA sequence, wherein said third DNA sequence has the DNA sequence:

5'ACAAXXX3' wherein X is a nucleotide base A, T, C or G.

9. The host cell of claim 6, wherein said first protein monomer has a DNA-binding domain cognate to said second DNA sequence, wherein said second DNA sequence has the DNA sequence:

5'ATTTAAGTT3' and wherein said second protein monomer has a DNA-binding domain cognate to said third DNA sequence, wherein said third DNA sequence has the DNA sequence:

5'ACAATAA3' wherein X is a nucleotide base A, T, C or G.

10. A method of regulating gene expression in a host cell, said host cell comprising a regulated expression construct comprising a gene, said gene comprising:

A) a first DNA sequence coding for a protein;
B) a DNA regulatory region operatively associated with said first DNA sequence, said DNA regulatory region having a protein-binding site consisting of adjacent different second and third DNA sequences on complementary strands; wherein the protein-binding site binds a heterodimer regulator protein; wherein said heterodimer protein consists of different first and second protein monomers which do not naturally form a heterodimer; and wherein i) said first protein monomer has a DNA-binding domain cognate to said second DNA sequence;
ii) said second protein monomer has a DNA-binding domain cognate to said third DNA sequence; and
iii) wherein said first and second protein monomers associate to form said heterodimer regulatory protein;

the method comprising supplying in said host cell a heterodimer comprising said first and second different protein monomers whereby when said heterodimer is bound to said protein-binding site, expression of said protein is regulated.

* * * * *